US007958889B1

(12) United States Patent
Fernandez-DeCastro

(10) Patent No.: US 7,958,889 B1
(45) Date of Patent: Jun. 14, 2011

(54) PROTECTIVE FACE COVER AND MOLDABLE ATTACHMENT

(75) Inventor: Aurora L. Fernandez-DeCastro, Union, MI (US)

(73) Assignee: Aurora L. Fernandez De Castro, Union, MI (US)

( * ) Notice: Subject to any disclaimer, the term of this patent is extended or adjusted under 35 U.S.C. 154(b) by 0 days.

(21) Appl. No.: 12/688,198

(22) Filed: Jan. 15, 2010

(51) Int. Cl.
*A61M 11/00* (2006.01)

(52) U.S. Cl. ......... 128/202.15; 128/205.27; 128/206.12; 128/206.19

(58) Field of Classification Search ............. 128/201.22, 128/201.23, 206.12–206.28, 207.11, 206.22, 128/202.15, 206.16, 206.29, 201.25, 201.29, 128/202.16, 205.25, 205.27
See application file for complete search history.

(56) References Cited

U.S. PATENT DOCUMENTS 2,023,267 A * 12/1935 De Saint Rapt et al. . 128/202.15
2,494,406 A 1/1950 Reitano
3,067,425 A * 12/1962 Colley ............................... 2/6.2
3,359,568 A * 12/1967 Kothe ............................... 2/410
4,328,797 A * 5/1982 Rollins et al. ............ 128/202.27
4,589,408 A 5/1986 Singer
4,823,785 A * 4/1989 Mancosu et al. ......... 128/202.15
4,827,923 A 5/1989 Bishop et al.
4,841,963 A * 6/1989 Vandeputte .............. 128/202.15
4,856,509 A 8/1989 Lemelson
4,890,609 A * 1/1990 Wilson, II ................ 128/206.29
4,941,470 A 7/1990 Hubbard et al.
4,974,586 A 12/1990 Wandel et al.
5,699,792 A 12/1997 Reese et al.
5,701,892 A 12/1997 Bledstein
5,717,991 A 2/1998 Nozaki et al.
5,735,270 A 4/1998 Bayer
5,819,731 A 10/1998 Dyrud et al.
6,055,982 A 5/2000 Brunson et al.
6,098,201 A 8/2000 Boros
6,123,077 A 9/2000 Bostock et al.
6,164,191 A * 12/2000 Liu et al. ......................... 99/305
6,213,125 B1 4/2001 Reese et al.
6,332,465 B1 12/2001 Xue et al.
6,394,090 B1 5/2002 Chen et al.
7,044,127 B1 5/2006 Fernandez DeCastro
7,320,722 B2 1/2008 Mittelstadt et al.
2009/0151734 A1 6/2009 Park

FOREIGN PATENT DOCUMENTS

CA 2269387 A1 10/2000
GB 2072516 A 10/1981

* cited by examiner

*Primary Examiner* — Steven O Douglas
(74) *Attorney, Agent, or Firm* — Browdy and Neimark, PLLC

(57) ABSTRACT

A protective face cover, mask or respirator with a moldable attachment that allows different devices or solids to be inserted into and withdrawn from inside the face cover of the wearer without removing it and the moldable attachment itself. The same moldable attachment can contain also an exhalation port to provide the mask with exhalation capability.

14 Claims, 5 Drawing Sheets

PROTECTIVE FACE COVER AND MOLDABLE ATTACHMENT

FIELD OF THE INVENTION

The present invention relates to a protective face cover, mask or respirator, with a moldable attachment that can be opened and closed to provide the insertion of devices for introducing liquid, solid materials or chemicals through an incision or aperture of the protective face cover, mask or respirator without removing it.

The present invention also relates to different types of moldable attachments that can be attachable to the protective face cover mask or respirator including moldable attachments containing additional exhalation port providing the face cover, mask or respirator with exhalation capacity.

BACKGROUND OF THE INVENTION

Filtration respirators, or face masks, have been widely used in the past to protect the respiratory system from particulate or chemical agents. These protective face covers are designed to minimize the transmission of contagious diseases or to protect the respiratory system from toxic substances or allergens in the surrounding atmosphere.

Protective face masks are generally used for preventing the transmission of contagious diseases, as well as to protect from inhalation of industrial or city dust or dirt, chemicals, allergens, and the like that may be present in the atmosphere. These masks are used to maintain a private, enclosed space around the breathing orifices when a person is in close proximity to other persons, or if an undesirable atmospheric agent is present. Additionally, infectious persons can wear masks to protect other people in the vicinity from their pathogens.

A variety of masks have been proposed which have different features, such as different ways of retaining the mask in place, providing different degrees of comfort for the wearer, having inhaling or exhausting valves, different types of seals around the mask for tighter sealing of the mask to the wearer's face. Other features include impregnating the mask with certain chemicals to make the mask more effective against air borne substances, and sterilizing the mask to enhance its cleanliness.

However, when the wearer wishes to eat or drink, the above masks must be removed so that food or drink can be imbibed. Of course, removing the mask means that the face is no longer protected. In addition, the mask may be misplaced, lost or contaminated.

Examples of some of these types of masks can be found in U.S. Pat. No. 2,494,406, which shows a protective mask which has elastic temple straps attached to the mask to enhance the conforming to the face of the wearer. In addition, U.S. Pat. No. 6,098,201 shows a molded face mask made of a plastic sheet in which a deformable wire is embedded so that the mask better conforms to the wearer's face.

U.S. Pat. No. 4,827,923 shows a protective facial mask that slips over the user's head.

U.S. Pat. No. 6,123,077 discloses a mask with a flat central panel to which other panels are joined through a fold line, seam, weld, or bond.

U.S. Pat. No. 4,974,586 shows a breathing mask which comprises an inhalation valve disposed in an opening of the wall of the mask. The inhalation valve opens at a sufficiently low breathing pressure to make it comfortable.

U.S. Pat. No. 5,699,792 shows a face mask with an enhanced facial seal.

U.S. Pat. No. 5,701,892 shows a two-sided chamber held away from the entrance of the nostrils and the mouth by a moldable support.

U.S. Pat. No. 4,941,470 shows a face mask having pleats formed therein and a method for fabricating the mask.

U.S. Pat. No. 6,394,090 shows a respiratory device having first and second lines of demarcation bisected by a fold so that the device can be folded.

U.S. Pat. No. 4,856,509 discloses a face mask containing a chemical or biological agent that destroys microorganisms such as viruses and bacteria.

U.S. Pat. No. 5,819,731 shows a face mask having a combination of adjustable ear loops and drop down band for a snug fit.

U.S. Pat. No. 5,717,991 shows a disposable sanitary mask comprising a cover panel section adapted to cover the wearer's nose and mouth and a pair of ear loops and panel sections to prevent the mask from losing its shape.

U.S. Pat. No. 5,735,270 discloses a disposable foldable face mask with face seal characteristics for a high efficiency filtering medium.

U.S. Pat. No. 6,213,125 discloses a device for protecting the face of the wearer including a gas pervious mask dimensioned to fit over the nose and mouth and a shield to protect the eyes of the wearer.

U.S. Pat. No. 6,332,465 discloses face masks having elastic polyolefin thermoplastic bands attached thereto by heat and pressure.

GB 2,072,516 discloses a face mask having one or more exhalation valves that flex so that the mask is completely closed during inhalation, and an opening is opened during exhalation.

U.S. Pat. No. 4,589,408 discloses a surgical face mask and hood that substantially completely surrounds the head of the wearer and reaches to the neck where it is fastened by a length of elastic. There is an opening for the eyes so that the wearer can see.

CA 2,269,387 describes a cold weather face mask that fits snugly on the face to cover the cheeks and nose of the wearer as well as the chin and jawbones.

U.S. Pat. No. 6,055,982 discloses a face mask which prevents transmission of air borne aerosols, particulate matter, and/or liquids, having an enhanced fluid barrier between the periphery of the mask and the wearer's face.

U.S. Pat. No. 7,044,127 discloses a face mask that has a self-closing opening through which the wearer can take nourishment or liquids without removing the mask.

Published Application No. 2009/0151734, discloses a combination mask and goggles having a replaceable filter over the mouth area that can be replaced without removing the plastic structure to which the removable filter is attached.

U.S. Pat. No. 7,320,722, discloses a respirating protection device to whish can be attached a source for clean air.

SUMMARY OF THE INVENTION

It is an object of the present invention to overcome aforesaid deficiencies in the prior art.

It is a further object of the present invention to provide a protective face cover, mask or respirator that need not be removed when the wearer wishes to eat or drink.

It is a further object of the present invention to provide for insertion of devices such as those providing food, drink and chemicals into the microenvironment behind the protective cover without removing it.

It is another object of the present invention to reproducibly manufacture a moldable attachment to provide some protection from the environment even when devices such as straws, tubes, sport caps, or other solids may be needed for the benefit of the wearer.

It is another object of the present invention to provide some protection from the environment when the wearer requires hydration, medications or nutrients.

It is another object of the present invention to provide a face cover that can be worn by the user for extended periods of time that are not limited to times not needed for sustenance of the wearer.

It is another object of the present invention to provide a face cover that provides a way to exhale at the times not needed for sustenance of the wearer to add convenience to the wearer during such times.

It is another object of the present invention that the moldable attachment can provide a better insertion of solids through the aperture of the face cover, which conforms or adapts to different size devices.

It is another object of the present invention that the moldable attachment have an exhalation port for more convenience or comfort to the wearer.

It is another object of the present invention that the protective face cover provide maximum protection, comfort and exhaling capability for prolonged periods while providing the wearer with sustenance when needed.

It is another object of the present invention that manufacturing only one moldable attachment can provide for different functions in the attachment itself.

It is another of the present invention to manufacture one moldable attachment that can combine benefits such as maximizing comfort, maximizing functions and maximizing the filtering area.

It is another object of the present invention to provide a protective face cover with the benefit of insertion of devices and solids, the comfort of exhalation and the maximum breathable filtering area for the wearer.

It is another object of the present invention that the moldable attachment can provide maximum closure when the mask is in the closed position.

It is a further object of the present invention that the face cover with moldable attachment can conform or accommodate devices of different sizes snugly minimizing air gaps surrounding devices of different sizes.

It is still another object of the present invention that the protective face cover provide maximum protection, comfort and exhalation capability while providing nutrition, chemicals and hydration to the wearer when needed while the wearer is still protected.

It is yet another object of the present invention to manufacture only one moldable attachment that can combine benefits such as maximizing comfort, maximizing functions, with minimal intrusion of the breathable area.

It is still another object of the present invention to provide a face mask that enables the wearer to receive hydration, medications and nourishment without removing the mask, and which makes it easy to discharge excess water vapor through an exhalation port.

BRIEF DESCRIPTION OF THE DRAWINGS

FIG. 5 is similar to FIG. 4 but shows more details of the exhalation port itself.

FIG. 5*a* shows the mask in the open position indicating the area of exhalation while

DETAILED DESCRIPTION OF THE INVENTION

Figure 1A:
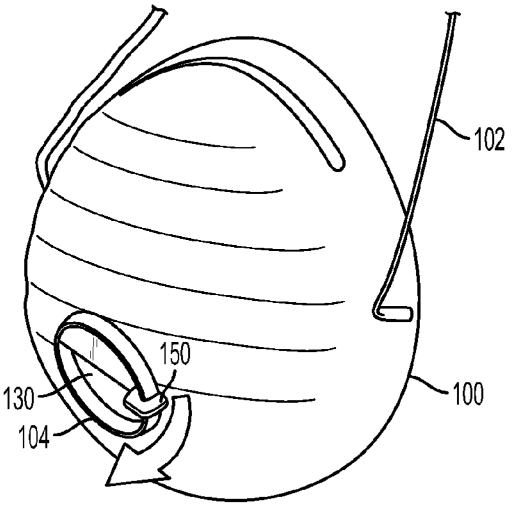
FIG. 1*a* shows a protective cover or mask with one style of moldable attachment in the open position.

Face covers, masks, respirators and the like have been used to protect the respiratory system from dust, particulates, odors and even microorganisms such as bacteria and viruses. For purposes of the present invention, "mask" includes all types of protectors for the face, mouth and/or nose, including respirators, face covers, and the like. The mask is generally made from filtering material having openings small enough to prevent the wearer from inhaling the undesired substances.

The present invention provides a mask having moldable attachment that is constructed so that it can be opened and closed at will to allow for insertion of devices such as straws, tubes, top-sports bottles, etc. for introducing liquids, solids, semisolids, chemicals or medicines, so that the wearer need not remove the mask during eating or drinking taking a pill or the like. While masks are known that have guarded openings, such as shown in U.S. Pat. No. 7,014,127, the entire contents of which are hereby incorporated by reference, the moldable attachment described here is more versatile and can accommodate a greater variety of inserted devices. The moldable attachment can fit over an opening such as in U.S. Pat. No. 7,014,127 in order to provide better protection of the wearer and better accommodating a variety of devices to provide hydration or nourishment, including straws of different sizes, spoons, forks, sports bottle mouths, and the like.

The moldable attachment can be opened and closed by different types of motion, such as rotation, sliding, flipping, and the like, nonlimiting examples of which are shown in FIGS. 1 through 4.

The moldable attachment can be made of any material that can be molded into a solid piece such as plastics, synthetic resin, saline resin, rubber, silicone or the like that can be molded to the desired shape and that can be attached to a mask or other type of face cover. The attachment to the face mask can be achieved by different means such as gluing, bonding, welding, snapping, etc.

In the present invention, the moldable attachment can also be molded so as to have an exhalation port or area on the top layer thereof. This is shown in FIGS. 1*f*, 2*f*, 3*f* and 4*f*. An exhalation port per se is shown in FIG. 5.

The moldable attachment can take any shape or form, and is not limited to the examples shown in the figures. Variations in the moldable attachment, such as shape, materials used for making it, materials to which they are attached, means of attachment and variations in the exhalation port area itself are all included within the scope of the present invention.

The perimeter with the conforming area can be achieved by a variety of ways to provide an adaptable fitting for devices of different sizes within the scope of the invention. It can also be treated with anti-infections or antiseptic agents within the scope of the invention.

FIGS. 1 to 4 illustrate masks that can be equipped with variations of a moldable attachment for permitting ingress of devices, liquids or solids into the mask without taking the mask off.

FIG. 1*a* shows a mask 100 having an elastic band 102 (or other means) for retaining the mask on the wearer's head. A moldable attachment 104 is provided near the mouth of the wearer on the mask. In FIG. 1*a*, the moldable attachment is in the open position so that opening 130 is provided for introduction of devices, food or liquids. The moldable attachment 104 can be closed by rotating the moldable attachment.

Figure 1B:
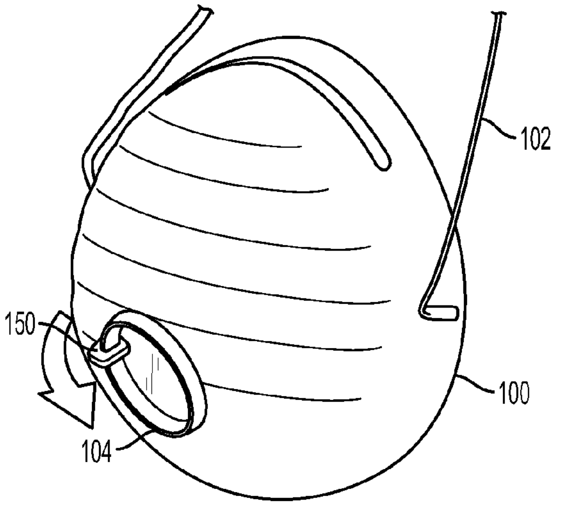
FIG. 1*b* shows the moldable attachment in the closed position.

FIG. 1*b* shows the mask with the moldable attachment 104 in the closed position. The attachment can be opened by rotating the moldable attachment in the direction opposite the direction for opening the moldable attachment.

Figure 1C:
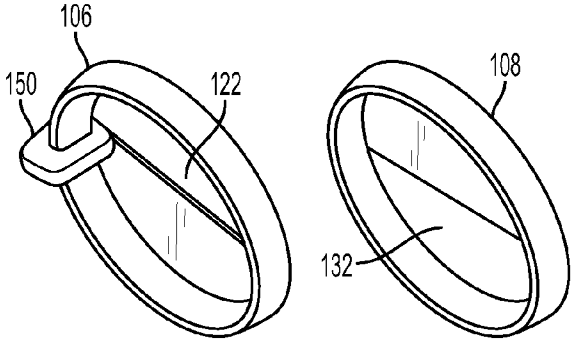
FIG. 1*c* shows two layers shown separated, which layers are shown as superimposed in FIG. 1*d*.

FIG. 1*c* shows the top layer 106 and the bottom layer 108 that form the moldable attachment. The opening 122 in the top layer 106 can be made to expose the opening 132 in the bottom layer 108 by rotating the top layer until the openings are both in the same position. A handle or knob 150 to aid opening and closing functions is shown.

Figure 1D:
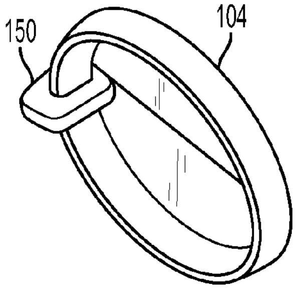
FIG. 1*e* shows a solid perimeter with a conforming area to minimize air inserted through the aperture of the moldable attachment. The perimeter can be placed before the filtering material of the mask or behind the mask material and can also serve for attachment of the moldable attachment to the mask. This applies as well to FIGS. 2*e*, 3*e* and 4*e*. The conforming area can also be chemically treated with anti infections agents.
FIG. 1*f* shows the moldable attachment of this style with an exhalation port or area.

FIG. 1*d* shows the two layers superimposed to form the moldable attachment 104 in the closed position. In this embodiment, the top layer is turned to close the mask so that the opening in the top layer 122 and in the bottom layer 132 are on opposite sides. A knob or handle to open and close the moldable attachment 150 is shown.

Figure 1E:
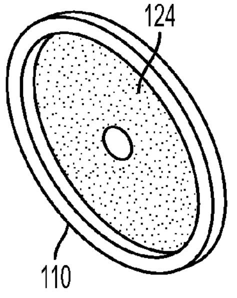

FIG. 1*e* shows a moldable perimeter 110 with a conforming area 124 in the middle. The conforming area allows for a snug fit when devices of different sizes are inserted into the moldable attachment itself. One way of usage is that the perimeter is located behind the mask while the moldable attachment is in front of the mask. By snapping, the moldable attachment is affixed to the mask. There are other means of attachment of the moldable attachment or the perimeter, such as gluing, bonding, welding, etc., all of which are within the scope of the invention. The mask has an incision or aperture not shown behind the moldable attachment though which the devices are inserted for hydration or nutrition.

Figure 1F:
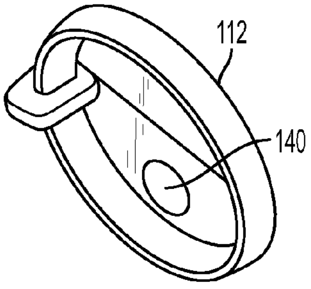

FIG. 1*f* shows the moldable attachment closed 112 with exhalation port. The exhalation port 140 is shown on the upper layer of the moldable attachment.

Figure 2A:
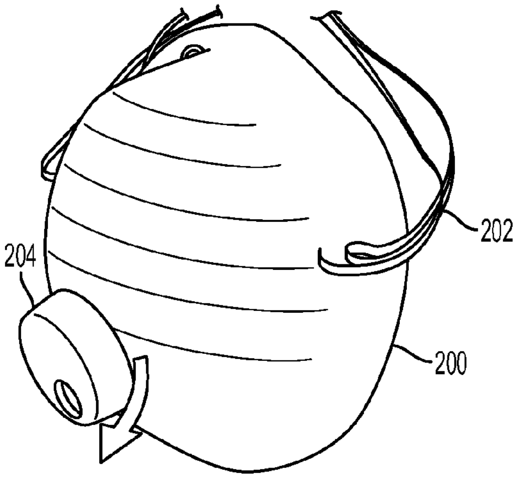
FIG. 2*a* shows a protective cover or mask with another style of moldable attachment in the open position.
Figure 2B:
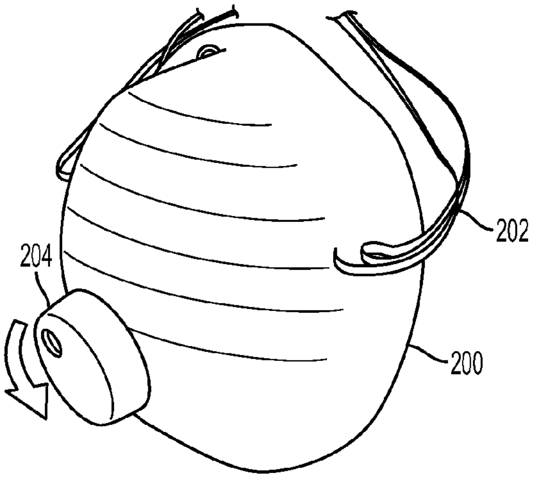
FIG. 2*b* shows the moldable attachment in the closed position.
Figure 2C:
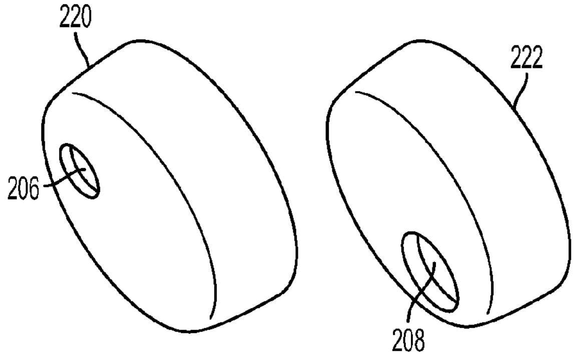
FIG. 2*c* shows the two separate layers of this style of attachment.

FIG. 2*a* shows another embodiment of a mask 200 having one type of retention means 202 with a moldable attachment 204 formed from a top layer 220 and a bottom layer 222, shown in FIG. 2*c*. FIG. 2*a* shows the mask in the open position and 2*b* in the closed position.

FIG. 2*c* shows the top layer 220 with an opening 206 and a bottom layer 222 with an opening 208. The layers are shown separated. When the moldable attachment 204 is in place, the top layer 220 can be rotated so that the openings in the top 206 and bottom layers match and the moldable attachment is open.

Figure 2D:
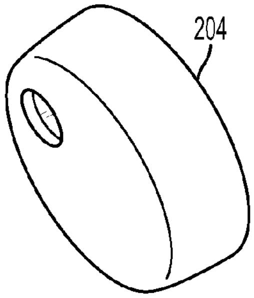
FIG. 2*d* shows the layers superimposed.

FIG. 2*d* shows the top layer 220 and the bottom layer 222 superimposed when openings 206 and 208 are not on top of one another or do not match and therefore the moldable attachment 204 is closed.

Figure 2E:
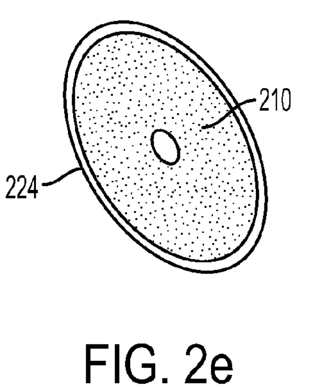
FIG. 2*e* shows a solid perimeter with a conforming area that can adapt or accommodate devices of different sizes when inserted through the aperture of the moldable attachment with better fitting.

FIG. 2*e*, shows a moldable perimeter 224 with a conforming area 210 that can be attached to the mask to provide a snug fit for devices of different sizes. The main purpose of the conforming area is to minimize air spaces when different size devices are inserted. In addition, it can also be used for attachment of the moldable to the mask by snapping the moldable attachment 204 over the perimeter 224. The mask in between has an incision or opening (not shown) through which the devices are inserted. Also, this piece can be a part of the moldable attachment in front of the mask material.

There are a variety of other ways of attaching the moldable attachment to the mask without changing the invention, including gluing, bonding, etc. that are well known to the skill in the art.

Figure 2F:
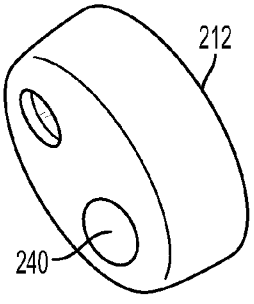
FIG. 2*f* shows this style of moldable attachment with an exhalation port or area as part of the moldable attachment. This conforming area can be treated with anti-infections agents or antiseptic agents.

FIG. 2*f* shows a closed moldable attachment 212 with an exhalation port or area 240 on the top layer. Details of the exhalation port are shown in FIG. 5. Moldable attachment 212 is the moldable attachment 204 with the exhalation area.

Figure 3A:
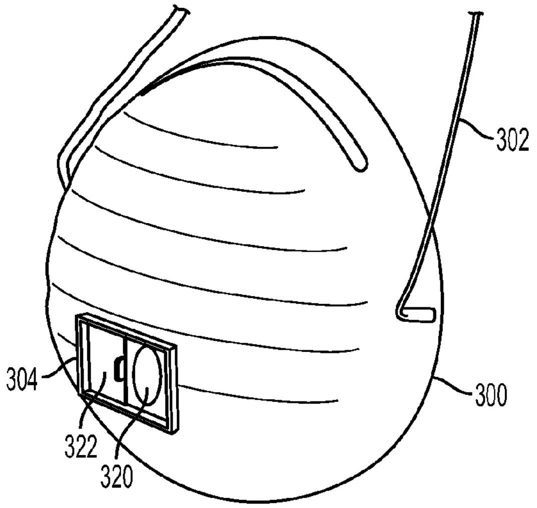
FIG. 3*a* shows a protective cover or mask with yet another style of moldable attachment in the open position.
Figure 3B:
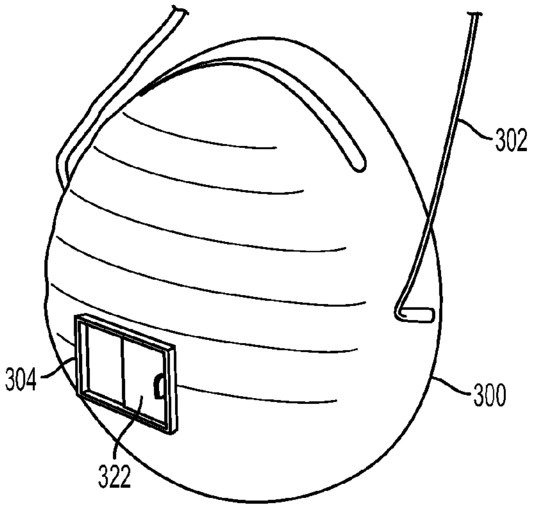
FIG. 3*b* shows the moldable attachment in the closed position. The non-rotational style of this attachment uses a sliding or translational motion to open and close. The sliding motion can be horizontal or vertical in this style.

FIGS. 3*a* and 3*b* show another embodiment of a moldable attachment 304 on a mask 300 with a retaining device 302. Other types of retaining devices can be used. FIG. 3*a*, shows the mask in the open position while FIG. 3*b* shows the mask in the closed position. Other numbers shown are described below.

Figure 3C:
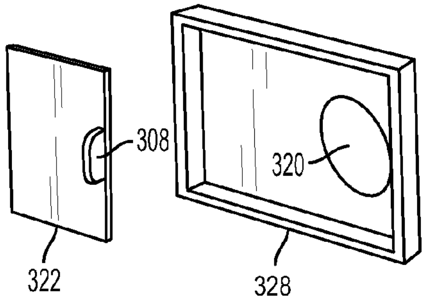
FIG. 3*c* shows the top and bottom layers of the moldable attachment separated.

FIG. 3*c* shows the two layers of this style. The upper layer 322 with a handle or knob 308 and a bottom layer 308. The bottom layer has an opening 320 that can be exposed or hidden as the upper layer 322 slides over the bottom layer 328. The sliding or transitional motion could be horizontal or vertical without changing the style.

Figure 3D:
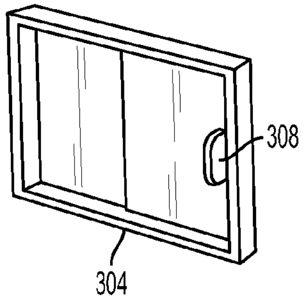
FIG. 3*d* shows the layers superimposed.

FIG. 3*d* shows moldable attachment 304 in the closed position. The upper layer 322 was moved to the right to close aperture 320.

Figure 3E:
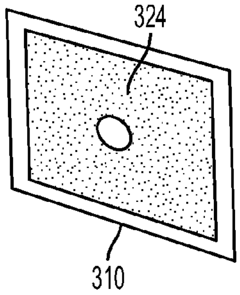
FIG. 3*e* shows a perimeter with a conforming area for better fitting of different size devices. The perimeter can be a part of the moldable attachment, attached to the moldable attachment or behind the mask, serving as an attachment for the moldable attachment and the mask.

FIG. 3*e* shows a moldable perimeter 310 with a conforming area 324 that can provide a snug fit to devices of different sizes while minimizing air leaks. This perimeter and conforming area can be a part of the moldable attachment itself or can be used to attach the moldable attachment to the mask. To attach the moldable attachment the perimeter 310 with area 324 is placed inside the mask and the moldable attachment outside the mask with the mask between the two layers. By snapping them together, the moldable attachment attaches to the mask. There are other ways of attachment the moldable attachment without changing the scope of the invention, which ways are well known to those skilled in the art.

Figure 3F:
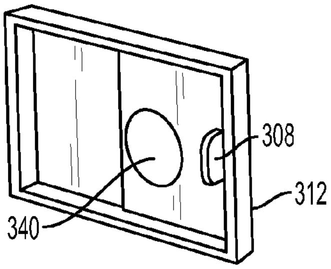
FIG. 3*f* shows this moldable attachment style with an exhalation port or area to provide exhalation capability to the mask.

FIG. 3*f* shows the moldable attachment 312 with an exhalation port 340. That is, the moldable attachment of this style 304 becomes 312 when it contains exhalation capabilities.

Figure 4A:
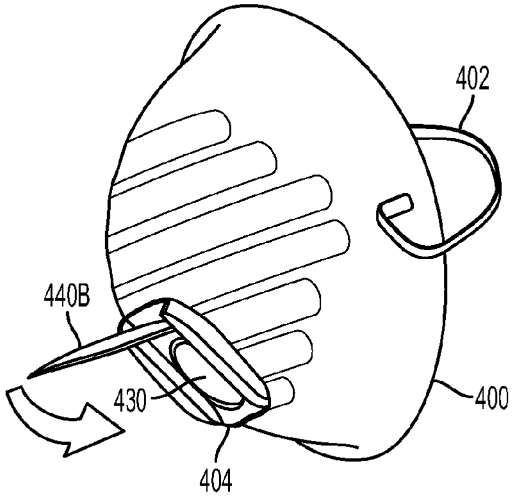
FIG. 4*a* shows a protective cover or mask with yet another style of moldable attachment in the open position.
Figure 4B:
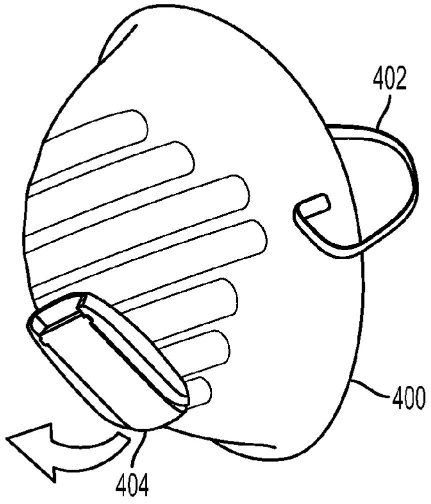
FIG. 4*b* shows the mask with the moldable attachment in the closed position.

FIGS. 4*a* and 4*b* show another embodiment of a moldable attachment 404 on a mask 400 with an example of a mask retaining device 402. FIG. 4*a* shows the mask in the open position while FIG. 4*b* shows the mask in the closed position. FIG. 4*a* shows the top part 440B of this style can turn or flip open showing an aperture 430.

Figure 4C:
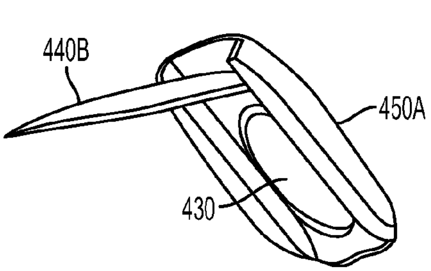
FIG. 4*c* shows, a top part and a bottom part, the two parts of the moldable attachment in the open position.
Figure 4D:
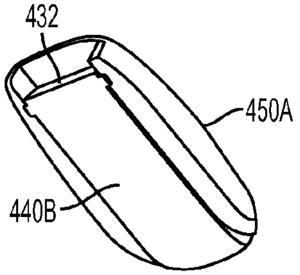
FIG. 4*d* shows the two parts of the moldable attachment in the closed position.

FIG. 4*c* shows the moldable attachment of this style. It is composed of a bottom layer 450A with an aperture 430 and a top layer 440B. The top layer 440B can be flipped or turned to open or close the moldable attachment. FIG. 4*c* shows the moldable attachment in the open position while FIG. 4*d* shows it in the closed position. FIG. 4*d* also shows an area of attachment 432 of the top and bottom layers. The area of attachment can be on the top, bottom or sides while maintaining a flipping or turning style referred to here. The attachment can be a hinge or other ways of attachment. The style can also have an area to lock or secure the top layer when closed.

Figure 4E:
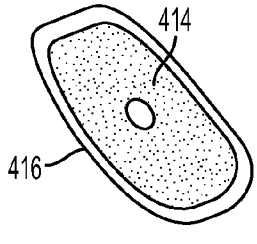
FIG. 4*e* shows a perimeter with conforming area for better adapting, accommodating or fitting of devices of different sizes through the aperture of the moldable attachment if needed. The conforming area can be placed after the aperture but before the filtering material of the mask or after the filtering material behind the mask. The perimeter can also be used for attachment of the moldable attachment to the mask. The conforming area can additionally be treated with anti-bacterial or anti-infections agents without changing the invention.

FIG. 4*e* shows a moldable perimeter 416 with a conforming area 414 within the perimeter to better fit around different size devices such as straws, tubes, etc. If placed behind the mask material it can be used for snapping to the moldable attachment. The perimeter with conforming area can be also be part of the moldable attachment itself and be then in front of the mask material.

Figure 4F:
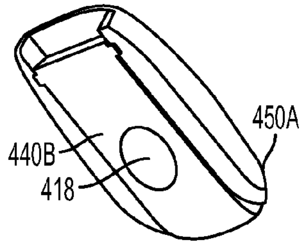
FIG. 4*f* shows this style of moldable attachment with exhalation capability port or area as part of the moldable attachment providing the mask with exhalation capability.

FIG. 4*f* shows this moldable attachment style closed with the exhalation area or port 418 on the top layer 440B resting on the bottom layer 450A, the normal closed position. In order to show more details of the exhalation port or area common to all styles, as shown in FIGS. 1*f*, 2*f*, 3*f*, the style of FIG. 4 was selected for FIG. 5.

Figure 5A:
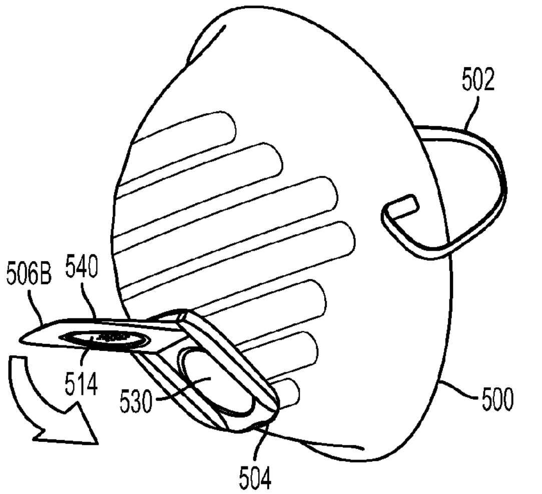
FIG. 5*a* is a protective cover or mask with the same style of moldable attachment shown in FIG. 4*a* but indicating the exhalation port or area on the top part or cover.

FIG. 5*a* shows a mask 500 with retaining device 502 and moldable attachment 504. This moldable attachment is the same style as 404 except with exhaling capability. The top layer of this moldable attachment is shown as 506B, the opening of the lower part of the exhalation port 514 and the upper part of the exhalation port 540. The mask is in the open position.

Figure 5B:
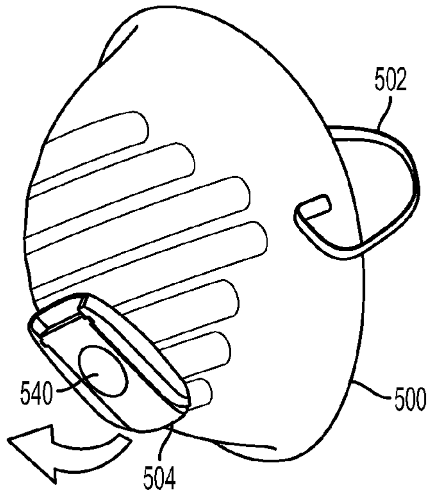
FIG. 5*b* shows the mask in the closed position also indicating the area of exhalation in the center of the upper or top part of the cover. The exhalation area has an area of aperture or apertures, for exhaling, and a membrane over it to close the openings when inhaling. Aperture(s), membrane and membrane guards are part of the exhalation area.

FIG. 5*b* shows the mask 500 in the closed position with moldable attachment 504. The upper part of the exhalation port 540 is shown.

Figure 5C:
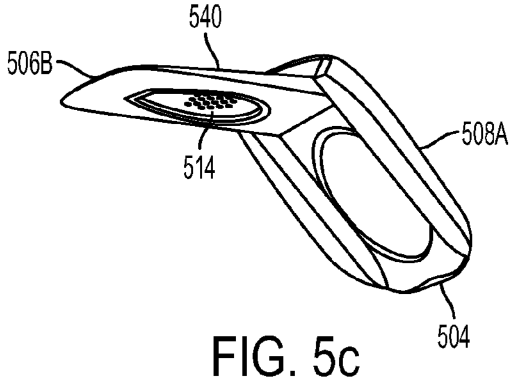
FIG. 5*c* shows the moldable attachment itself in the open position showing the exhalation area on the upper part of the moldable attachment.

FIG. 5*c* shows the two parts of the style, the upper part 506B and the bottom part 508B with more detail of the exhalation port. The figure shows the exhalation port on the top layer 506B of the moldable attachment 504. The top part of the exhalation port is indicated as 540 and the bottom part as 514. The bottom part 514 has one opening or several openings for exhalation and a top part 540 with a membrane that closes the openings when inhaling.

Figure 5D:
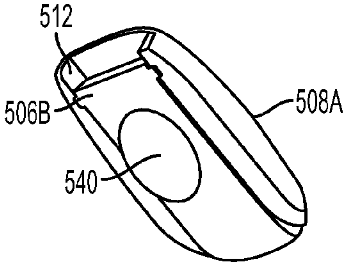
FIG. 5*d* shows the moldable attachment itself in the closed position showing the membrane that covers the opening area (several openings shown but it can be one opening only) of the exhalation port. A membrane guard for protection of the membrane is indicated. This membrane guard can be varied so as to provide protection to the exhalation membrane. The exhalation port or area mentioned throughout encompasses opening(s), membrane covering the opening(s) and membrane guard(s) for protecting the membrane.

FIG. 5*d* shows the moldable attachment 504 closed as the top part 506B is over the bottom part 508A. The membrane of the exhalation port is shown as 540. The attachment of the top layer 506B and the bottom layer 508A is shown as 512. Different types of attachments are possible. Also, different ways of assuring closure are possible.

Figure 5E:
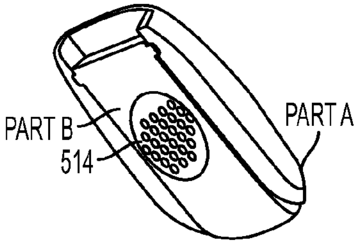
FIGS. 5*e* and 5*f* show the details of the exhalation area or port common to all exhalation areas of FIGS. 1 through 4. To avoid repetition the details are shown only with the style of FIG. 4.

FIG. 5*e* shows the top layer 506B as part B and the bottom layer 508A as part A. The middle area 514 on the top layer shows the openings (it could be only one) that are part of the exhalation port. The membrane is not shown in this figure but is shown in the next figure.

Figure 5F:
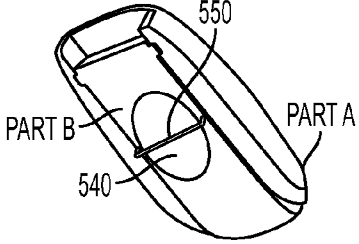

FIG. 5*f* shows the closed moldable attachment 504 with the membrane 540 of the exhalation port which covers the openings 514 of the previous figure. The figure also shows a guard 550 placed on top of the membrane for protection. This membrane guard can have different shapes or form within the invention.

The exhalation port referred to throughout the different styles is composed of opening or openings, membrane and membrane guard on the top layer, which can be used to exhale when the moldable attachments are closed.

All the examples above show protective face covers, masks or respirators with a moldable attachment that can be opened or closed for the insertion of devices, nutrients or solids without removing the mask and that can exhaust or exhale air out from within the mask. They also show a way of snug fitting devices of different size with a conforming area. The conforming area may or may not be treated with chemicals or antiinfective agents. The moldable attachment may contain several functions maximizing the filtering or breathing areas. Variations of the moldable attachment such as shape, constructing materials, shape or type of filtering material or means of attachment to the mask, respirator or face cover are not materially different from what is hereby disclosed.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

What is claimed is:

1. A protective face cover made of a filtering material adapted and constructed to cover at least the mouth and nose of the wearer, and a moldable attachment having an opening that can be opened and closed at will for introduction of devices that carry nourishment, liquids or chemicals to the wearer through the opening in the moldable attachment without removing the protective face cover, wherein said moldable attachment consists of at least one layer superimposed on the mask, each layer having an opening that rotates or slides or is exposed by raising a covering layer to expose an opening in the moldable attachment.

2. The protective face cover according to claim 1 further including an exhalation port contained in the moldable attachment.

3. The protective face cover according to claim 1, further including conforming area behind the opening of the moldable attachment.

4. The protective face cover according to claim 1, wherein the moldable attachment consists of two layers superimposed on each other, each of said layers having an opening, that rotate to expose an opening in the moldable attachment.

5. The protective face cover according to claim 4, wherein the moldable attachment has an exhalation port.

6. The protective face cover according to claim 4, wherein the face cover includes a conforming area behind the opening in the moldable attachment.

7. The protective face cover according to claim 1, wherein the moldable attachment consists of moldable layers each layer having an opening and solid area that can slide to expose an opening in the moldable attachment through which devices can be inserted.

8. The protective face cover according to claim 7, wherein the moldable attachment includes an exhalation port.

9. The protective face cover according to claim 7, wherein the face cover includes a conforming area behind the opening in the moldable attachment.

10. The protective face cover according to claim 1, wherein the moldable attachment consists of a base and a cover that can flip or turn to expose the opening in the moldable attachment through which devices can be inserted.

11. The protective face cover according to claim 10, wherein the moldable attachment has an exhalation port.

12. The protective face cover according to claim 10, wherein the face cover has a conforming area behind the opening of the moldable attachment.

13. The face cover according to claim 1, wherein the moldable attachment is attached to the face cover by inserting the face cover between the moldable attachment and a moldable perimeter, and snapping the moldable attachment over the moldable perimeter.

14. The face cover according to claim 1, wherein the moldable attachment is attached to the face cover by inserting the face cover between the moldable attachment and a moldable perimeter with conforming area, and snapping the moldable attachment over the moldable perimeter with conforming area.

* * * * *